US011567533B2

(12) United States Patent
Kim et al.

(10) Patent No.: US 11,567,533 B2
(45) Date of Patent: Jan. 31, 2023

(54) ELECTRONIC DEVICE INCLUDING BIOSENSOR AND KEY STRUCTURE FOR ELECTRODE

(71) Applicant: Samsung Electronics Co., Ltd., Gyeonggi-do (KR)

(72) Inventors: Kijung Kim, Gyeonggi-do (KR); Youngjae Ko, Gyeonggi-do (KR); Junghyun Kang, Gyeonggi-do (KR); Taegyun Kim, Gyeonggi-do (KR); Jaejong Ryu, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 85 days.

(21) Appl. No.: 17/139,010

(22) Filed: Dec. 31, 2020

(65) Prior Publication Data

US 2021/0208624 A1 Jul. 8, 2021

(30) Foreign Application Priority Data

Jan. 3, 2020 (KR) .................. 10-2020-0000951

(51) Int. Cl.
*G06F 1/16* (2006.01)
(52) U.S. Cl.
CPC ............ *G06F 1/163* (2013.01); *G06F 1/1633* (2013.01); *G06F 1/1637* (2013.01)
(58) Field of Classification Search
CPC ...... G06F 1/163; G06F 1/1633; G06F 1/1637; A61B 5/02438; A61B 5/681; A61B 5/6824; A61B 5/6831
See application file for complete search history.

(56) References Cited

U.S. PATENT DOCUMENTS

| 7,407,386 | B1 * | 8/2008 | Ichikawa | ............. H05K 3/3452 |
| | | | | 439/55 |
| 9,844,340 | B2 | 12/2017 | Fish et al. | |
| 9,924,003 | B2 | 3/2018 | Jun et al. | |
| 10,539,700 | B1 * | 1/2020 | Sepänniitty et al. | . G06F 1/1656 |
| 10,962,935 | B1 * | 3/2021 | Ely | ........................ G06F 3/0362 |
| 11,181,863 | B2 * | 11/2021 | Ely | ........................ G04G 21/08 |

(Continued)

FOREIGN PATENT DOCUMENTS

| KR | 10-2017-0008197 A | 1/2017 |
| KR | 10-2017-0046542 A | 5/2017 |

*Primary Examiner* — Nidhi Thaker
(74) *Attorney, Agent, or Firm* — Cha & Reiter, LLC

(57) ABSTRACT

An electronic device is disclosed, including a housing including a first surface forming a front surface of the electronic device, a second surface facing away from the first surface, and a side surface surrounding an interior space defined between the first surface and the second surface, a key structure forming part of the side surface and extending into the interior space, the key structure including an electrode member partially exposed to an exterior environment, wherein the electrode member partially extends into the interior space, a display disposed in the housing so as to be visible through the first surface from the exterior environment, an internal structure disposed between the display and the second surface, wherein the internal structure includes a printed circuit board, and a conductive structure protruding from the internal structure, wherein the conductive structure is electrically connected with the electrode member of the key structure.

15 Claims, 11 Drawing Sheets

(56) References Cited

U.S. PATENT DOCUMENTS

| | | | |
|---|---|---|---|
| 2016/0254587 A1* | 9/2016 | Jung | H01Q 7/00 |
| | | | 343/702 |
| 2017/0296088 A1* | 10/2017 | Choi | A61B 5/7271 |
| 2018/0024683 A1* | 1/2018 | Ely | G04C 3/007 |
| | | | 345/174 |
| 2018/0173279 A1* | 6/2018 | Park | G06F 1/1656 |
| 2020/0064779 A1* | 2/2020 | Pandya | G06F 1/1626 |
| 2020/0073339 A1* | 3/2020 | Roach | G04G 17/08 |

* cited by examiner

ELECTRONIC DEVICE INCLUDING BIOSENSOR AND KEY STRUCTURE FOR ELECTRODE

CROSS-REFERENCE TO RELATED APPLICATION(S)

This application is based on and claims priority under 35 U.S.C. § 119 to Korean Patent Application No. 10-2020-0000951, filed on Jan. 3, 2020, in the Korean Intellectual Property Office, the disclosure of which is incorporated by reference herein its entirety.

BACKGROUND

1. Field

The disclosure relates to an electronic device including a biosensor and a key structure for an electrode. More particularly, the disclosure relates to a wearable electronic device capable of detecting biometric information.

2. Description of Related Art

With the popularization of portable devices such as smartphones, the use of paired wearable devices (e.g., smart watches, and the like) in conjunction with smartphones has increased. The wearable devices may be connected with the smartphones through wired or wireless communication and may provide users with various functions or operations provided by or integrated with the smartphone. Due to the convenience facilitated between these two devices, the spread of wearable devices has been on the rise.

Atrial fibrillation ("AFib") is one of the most common cardiac arrhythmias, having a prevalence rate of about 2% of the general public in developed countries. The existence of AFib may potentially lead to serious health risks.

The above information is presented as background information only to assist with an understanding of the disclosure. No determination has been made, and no assertion is made, as to whether any of the above might be applicable as prior art with regard to the disclosure.

SUMMARY

AFib may be detected by an electrocardiogram (ECG). An ECG-based approach achieves very high accuracy in the detection of AFib, but requires a complicated device having a plurality of electrodes for observation of ECG signals.

Recently, photoplethysmography (PPG) has been presented as an alternative to ECG in the detection of AFib. A PPG-based solution has the advantage that PPG signals can be easily recorded and observed from consumer-level wearable devices without active efforts of participants. Due to the above advantage, user-friendly AFib observation and detection on a daily basis may be spread to general users by using available wearable devices and smartphones. This may lead to beneficial effects on the population affected by AFib.

For measurement of an electrocardiogram, a wearable electronic device requires a conductive area exposed on a side surface of the wearable electronic device and a connecting structure for connecting the conductive area and a sensor in the wearable electronic device.

Aspects of the disclosure are to address at least the above-mentioned problems and/or disadvantages and to provide at least the advantages described below. Accordingly, an aspect of the disclosure is to provide an electronic device that includes a connecting structure considering a limited interior space of the electronic device and an electrode member considering interference with an antenna.

In accordance with an aspect of the disclosure, an electronic device includes a housing including a first surface forming a front surface of the electronic device, a second surface facing away from the first surface, and a side surface surrounding an interior space defined between the first surface and the second surface, a key structure forming part of the side surface and extending into the interior space, the key structure including an electrode member partially exposed to an exterior environment, wherein the electrode member partially extends into the interior space, a display disposed in the housing so as to be visible through the first surface from the exterior environment, an internal structure disposed between the display and the second surface, wherein the internal structure includes a printed circuit board, and a conductive structure protruding from the internal structure, wherein the conductive structure is electrically connected with the electrode member of the key structure.

Other aspects, advantages, and salient features of the disclosure will become apparent to those skilled in the art from the following detailed description, which, taken in conjunction with the annexed drawings, discloses certain embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

With regard to description of the drawings, identical or similar reference numerals may be used to refer to identical or similar components.

DETAILED DESCRIPTION

Hereinafter, certain embodiments of the disclosure will be described with reference to the accompanying drawings. However, those of ordinary skill in the art will recognize that modifications, equivalents, and/or alternatives on the certain embodiments described herein can be variously made without departing from the disclosure.

Figure 1:
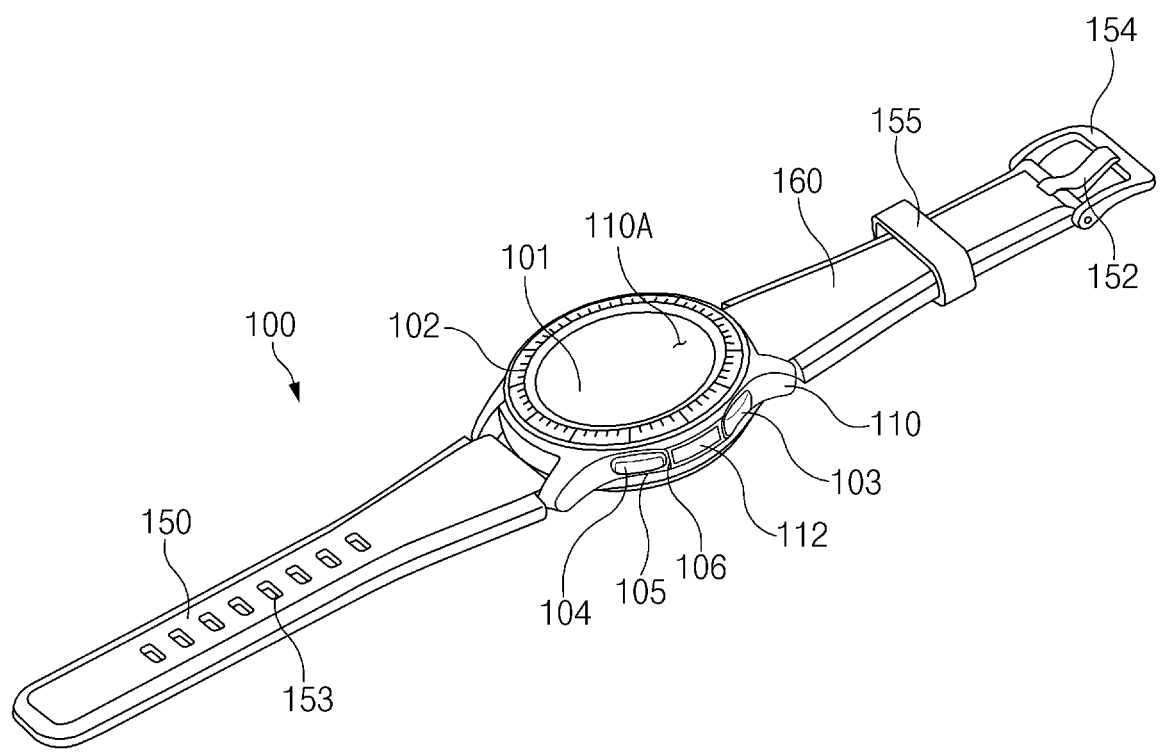
FIG. 1 is a front perspective view of an electronic device according to an embodiment.
Figure 2:
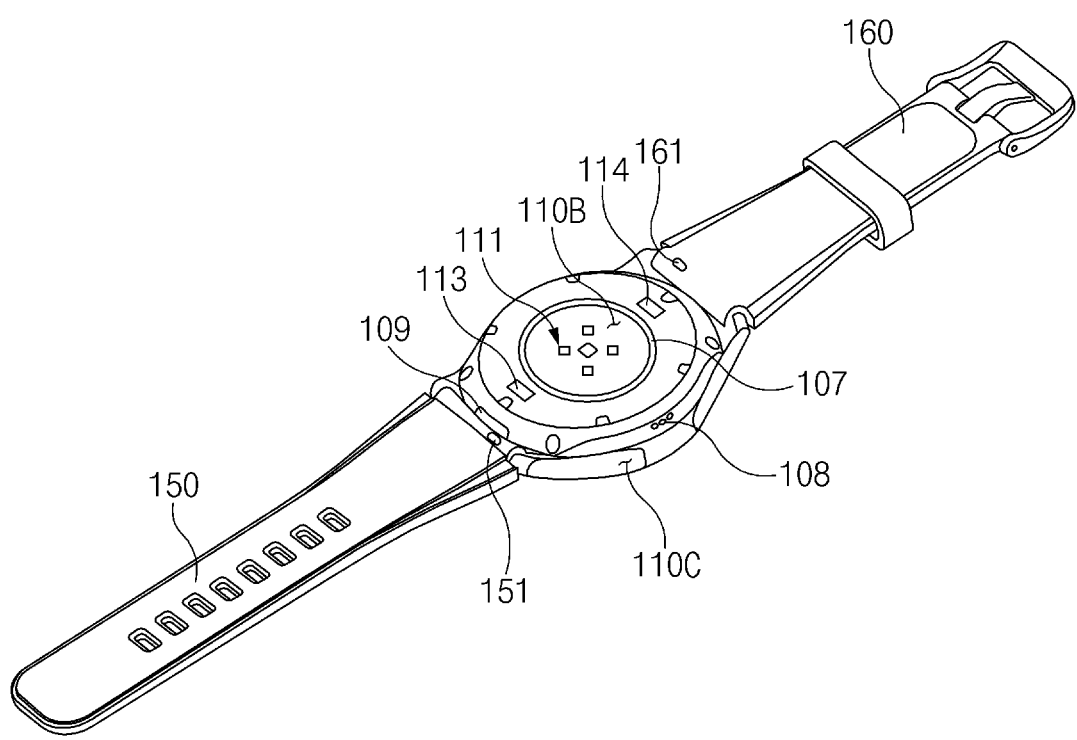
FIG. 2 is a rear perspective view of the electronic device according to an embodiment.

FIG. 1 is a front perspective view of an electronic device according to an embodiment. FIG. 2 is a rear perspective view of the electronic device according to an embodiment.

Referring to FIGS. 1 and 2, the electronic device 100 according to an embodiment may include a housing 110 and fastening members 150 and 160. The housing 110 may include a first surface (or, a front surface) 110A, a second surface (or, a rear surface) 110B, and a side surface 110C surrounding a space between the first surface 110A and the second surface 110B, and the fastening members 150 and 160 may be connected to at least parts of the housing 110 and may be configured to detachably fasten the electronic device 100 on a part (e.g., a wrist, an ankle, or the like) of a user's body. In another embodiment (not illustrated), a housing may refer to a structure that forms some of the first surface 110A, the second surface 110B, and the side surface 110C of FIG. 1. According to an embodiment, the first surface 110A may be formed by a front plate 101, at least part of which is substantially transparent (e.g., a glass plate including various coating layers, or a polymer plate). The second surface 110B may be formed by a back plate 107 that is substantially opaque. The back plate 107 may be formed of, for example, coated or colored glass, ceramic, polymer, metal (e.g., aluminum, stainless steel (STS), or magnesium), or a combination of at least two of the aforementioned materials. The side surface 110C may be formed by a side bezel structure (or, a "side member") 106 that is coupled with the front plate 101 and the back plate 107 and that contains metal and/or polymer. In some embodiments, the back plate 107 and the side bezel structure 106 may be integrally formed with each other and may contain the same material (e.g., a metallic material such as aluminum). The fastening members 150 and 160 may be formed of various materials and may have various forms. The fastening members 150 and 160 may be formed of woven fabric, leather, rubber, urethane, metal, ceramic, or a combination of at least two of the aforementioned materials and may be implemented in an integrated form or with a plurality of unit links that are movable relative to each other.

According to an embodiment, the electronic device 100 may include at least one of a display 120 (refer to FIG. 3), audio modules 105 and 108, a sensor module 111, key input devices 102, 103, and 104, or a connector hole 109. In some embodiments, the electronic device 100 may omit at least one component (e.g., the key input devices 102, 103, and 104, the connector hole 109, or the sensor module 111) among the aforementioned components, or may additionally include other component(s).

The display 120 may be exposed through, for example, a large portion of the front plate 101. The display 120 may have a shape corresponding to the shape of the front plate 101. The display 120 may have various shapes such as a circular shape, an oval shape, a polygonal shape, or the like. The display 120 may be combined with, or disposed adjacent to, touch detection circuitry, a pressure sensor capable of measuring the intensity (pressure) of a touch, and/or a fingerprint sensor.

The audio modules 105 and 108 may be operatively coupled to microphone hole and the speaker hole. A microphone for obtaining a sound from the outside may be disposed in the microphone hole. In some embodiments, a plurality of microphones may be disposed in the microphone hole to detect the direction of a sound. The speaker hole may be used for an external speaker and a call receiver. In some embodiments, the speaker hole and the microphone hole may be implemented with a single hole, or a speaker (e.g., a piezo speaker) may be included without the speaker hole.

The sensor module 111 may generate an electrical signal or a data value that corresponds to an operational state inside the electronic device 100 or an environmental state external to the electronic device 100. The sensor module 111 may include, for example, a biosensor module 111 (e.g., an HRM sensor) that is disposed on the second surface 110B of the housing 110. The electronic device 100 may further include a non-illustrated sensor module, which may be, for example, at least one of a gesture sensor, a gyro sensor, an atmospheric pressure sensor, a magnetic sensor, an acceleration sensor, a grip sensor, a color sensor, an infrared (IR) sensor, a biosensor, a temperature sensor, a humidity sensor, or an illuminance sensor.

In an embodiment, the sensor module 111 may include electrode areas 112, 113, and 114 that form parts of a surface of the electronic device 100 and biosignal detection circuitry (not illustrated) that is electrically connected with the electrode areas 112, 113, and 114. For example, the electrode areas 112, 113, and 114 may include the first electrode area 112 disposed on the side surface 110C of the housing 110, and the second electrode area 113 and the third electrode area 114 that are disposed on the second surface 110B of the housing 110.

In certain embodiments, the sensor module 111 may be configured such that the electrode areas 112, 113, and 114 obtain electrical signals from a part of the user's body and the biosignal detection circuitry detects biometric information of the user based on the electrical signals.

The key input devices 102, 103, and 104 may include the wheel key 102 disposed on the first surface 110A of the housing 110. The wheel key 102 is rotatable in at least one direction and/or the side key buttons 103 and 104 disposed on the side surface 110C of the housing 110. The wheel key 102 may have a shape corresponding to the shape of the front plate 101. In another embodiment, the electronic device 100 may not include all or some of the aforementioned key input devices 102, 103, and 104, and the key input devices 102, 103, and 104 not included may be implemented in a different form such as a soft key on the display 120

The connector hole 109 may accommodate a connector (e.g., a USB connector) for transmitting and receiving electric power and/or data with an external electronic device and may include another connector hole (not illustrated) that accommodates a connector for transmitting and receiving audio signals with an external electronic device. The electronic device 100 may further include, for example, a connector cover (not illustrated) that covers at least part of the connector hole 109 and blocks infiltration of external foreign matter into the connector hole 109.

The fastening members 150 and 160 may be detachably fastened to at least partial areas of the housing 110 by locking members 151 and 161. The fastening members 150 and 160 may include one or more of a fixing member 152, fixing member fastening holes 153, a band guide member 154, and a band fixing ring 155.

The fixing member 152 may be configured to fix the housing 110 and the fastening members 150 and 160 to a part (e.g., a wrist, an ankle, or the like) of the user's body. The fixing member 152 may be fastened to one of the fixing member fastening holes 153 to fix the housing 110 and the fastening members 150 and 160 to the part of the user's body. The band guide member 154 may be configured to restrict a movement range of the fixing member 152 when the fixing member 152 is fastened to one of the fixing member fastening holes 153. Accordingly, the fastening members 150 and 160 may be fastened to the part of the user's body in a state of being brought into close contact with the part of the user's body. The band fixing ring 155 may restrict a movement range of the fastening members 150 and 160 in a state in which the fixing member 152 is fastened to one of the fixing member fastening holes 153.

Figure 3:
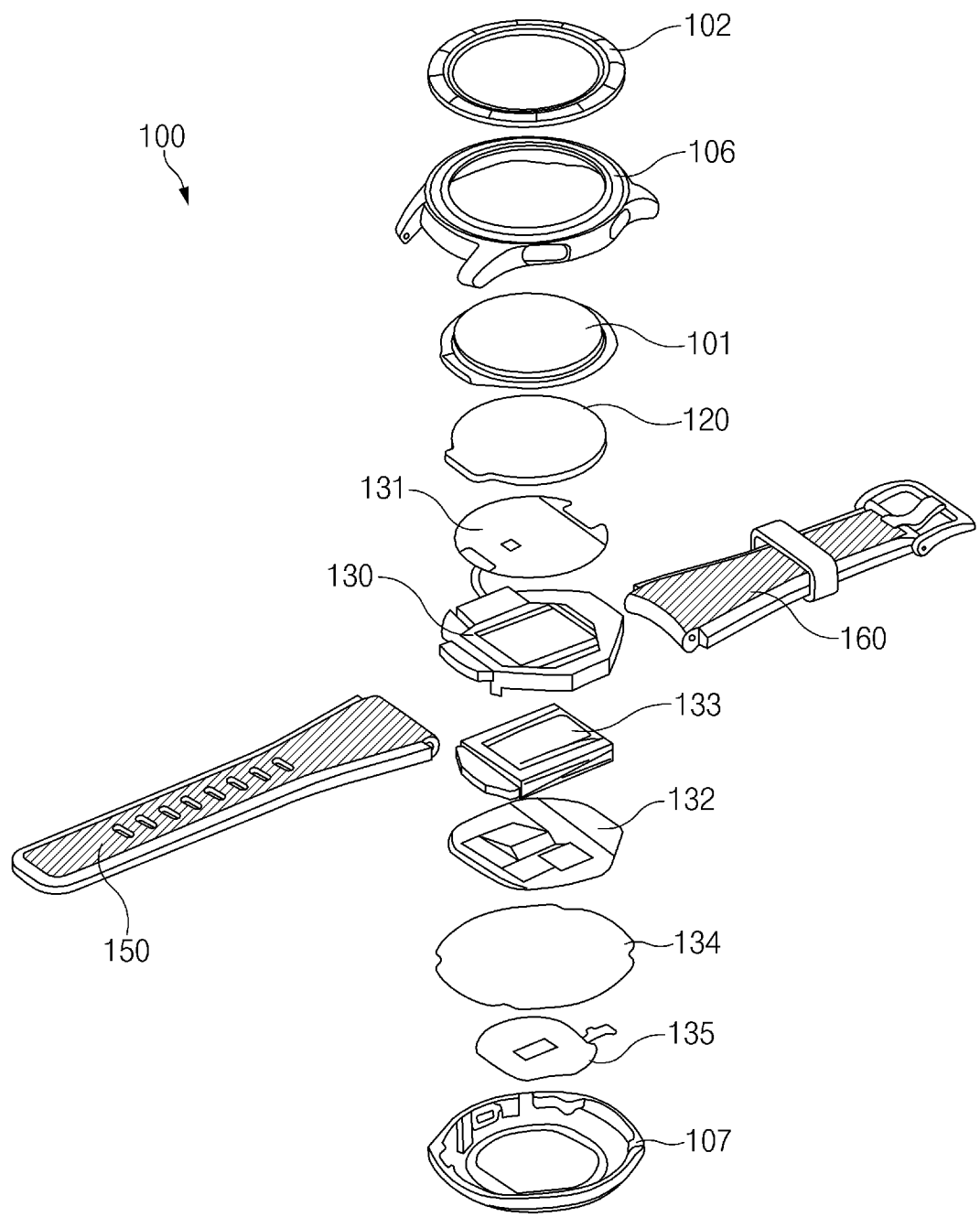
FIG. 3 is an exploded perspective view of the electronic device according to an embodiment.

FIG. 3 is an exploded perspective view of the electronic device according to an embodiment.

Referring to FIG. 3, the electronic device 100 may include the side bezel structure 106, the wheel key 102, the front plate 101, the display 120, a first antenna 131, a second antenna 135, a support member 130 (e.g., a bracket), a battery 133, a printed circuit board 132, a sealing member 134, the back plate 107, and the fastening members 150 and 160.

The support member 130 may be disposed inside the electronic device 100 and may be connected with the side bezel structure 106, or may be integrally formed with the side bezel structure 106. The support member 130 may be formed of, for example, a metallic material and/or a nonmetallic (e.g., polymer) material. The display 120 may be coupled to one surface of the support member 130, and the printed circuit board 132 may be coupled to an opposite surface of the support member 130. The printed circuit board 132 may have a processor, a memory, and/or an interface mounted thereon. The processor may include, for example, one or more of a central processing unit, an application processor, a graphic processing unit (GPU), a sensor processor, or a communication processor.

The memory may include, for example, a volatile memory or a nonvolatile memory. The interface may include, for example, a high definition multimedia interface (HDMI), a universal serial bus (USB) interface, an SD card interface, and/or an audio interface. For example, the interface may electrically or physically connect the electronic device 100 with an external electronic device and may include a USB connector, an SD card/MMC connector, or an audio connector.

The battery 133 may supply electric power to at least one component of the electronic device 100. The battery 133 may include, for example, a primary cell that is not rechargeable, a secondary cell that is rechargeable, and/or a fuel cell. At least part of the battery 133 may be disposed, for example, on substantially the same plane as the printed circuit board 132. The battery 133 may be integrally disposed inside the electronic device 100, or may be disposed so as to be detachable from the electronic device 100.

The first antenna 131 may be disposed between the display 120 and the support member 130. The first antenna 131 may include, for example, a near field communication (NFC) antenna, a wireless charging antenna, and/or a magnetic secure transmission (MST) antenna. The first antenna 131, for example, may perform short-range communication with an external device, or may wirelessly transmit and receive electric power used for charging, and may transmit an electromagnetic signal including a short-range communication signal or payment data. In another embodiment, an antenna structure may be formed by part of the side bezel structure 106 and/or part of the support member 130, or a combination thereof.

The second antenna 135 may be disposed between the printed circuit board 132 and the back plate 107. The second antenna 135 may include, for example, a near field communication (NFC) antenna, a wireless charging antenna, and/or a magnetic secure transmission (MST) antenna. The second antenna 135, for example, may perform short-range communication with an external device, or may wirelessly transmit and receive electric power used for charging, and may transmit an electromagnetic signal including a short-range communication signal or payment data. In another embodiment, an antenna structure may be formed by part of the side bezel structure 106 and/or part of the back plate 107, or a combination thereof.

The sealing member 134 may be located between the side bezel structure 106 and the back plate 107. The sealing member 134 may be configured to block moisture and foreign matter introduced from the outside into a space surrounded by the side bezel structure 106 and the back plate 107.

Figure 4:
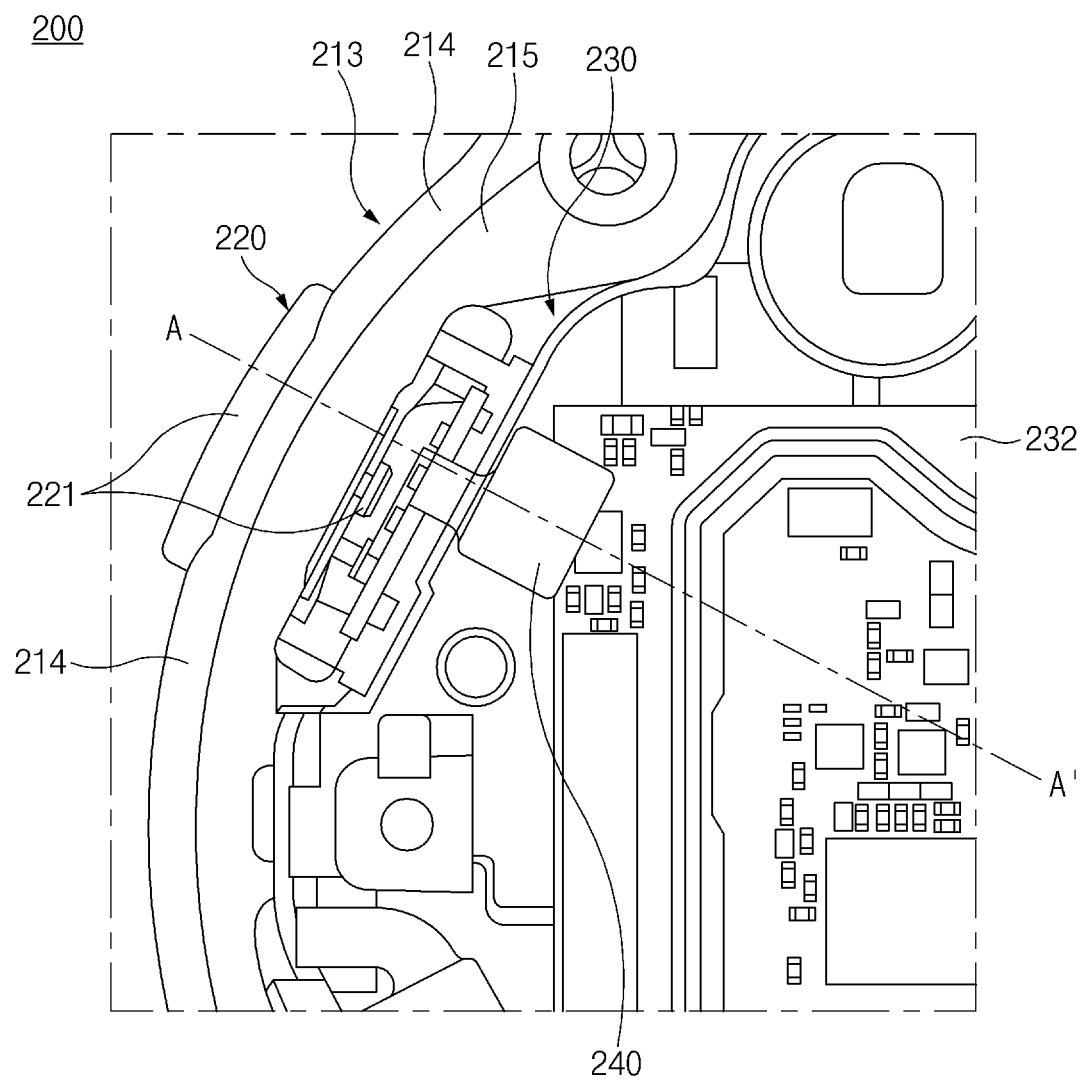
FIG. 4 is a plan view of an electronic device according to an embodiment.

FIG. 4 is a plan view of an electronic device according to an embodiment.

According to an embodiment, the electronic device 200 (e.g., the electronic device 100 of FIG. 1) may include a bracket 213, an internal structure 230, a printed circuit board 232, and a key structure 220.

In an embodiment, the bracket 213 may include a frame structure 214 that forms a side surface of the electronic device 200 and a plate structure 215 extending from the frame structure 214 into the electronic device 200. The frame structure 214 may surround an interior space of the bracket 213. The plate structure 215 may extend from the frame structure 214 toward the interior space of the bracket 213. The frame structure 214 may have a through-hole formed therein. Part of the key structure 220 may be disposed in the through-hole of the frame structure 214. In certain embodiments, the frame structure 214 of the bracket 213 may form a housing of the electronic device 200 (e.g., the housing 110 of FIG. 1) together with a first cover (e.g., the front plate 101 of FIG. 3) that forms a front surface of the electronic device 200 and a second cover (e.g., the back plate 107 of FIG. 3) that forms a rear surface of the electronic device 200.

In an embodiment, part of the key structure 220 may form part of the side surface of the electronic device 200, and the remaining part of the key structure 220 may extend into the bracket 213 through the through-hole of the frame structure 214. The key structure 220 may face the internal structure 230 located inside the bracket 213. The key structure 220 may include an electrode member 221. Part of the electrode member 221 included in the key structure 220 may be exposed on the side surface of the electronic device 200. The electrode member 221 may be connected with the printed circuit board 232, which is included in the internal structure 230, by a connecting member 240. The electrode member 221 may be electrically connected with biosignal detection circuitry on the printed circuit board 232 by the connecting member 240.

In an embodiment, the internal structure 230 may be disposed in the interior space of the bracket 213. The internal structure 230 may include at least one of the printed circuit board 232, a battery (e.g., the battery 133 of FIG. 3), or an antenna (e.g., the antennas 131 and 135 of FIG. 3). The internal structure 230 may include a sidewall (e.g., a sidewall 231 of FIG. 5) that faces the frame structure 214.

In an embodiment, the connecting member 240 may be configured to electrically connect the electrode member 221, which is included in the key structure 220, and the printed circuit board 232. The connecting member 240 may include a flexible printed circuit board.

In certain embodiments, the electronic device 200 may further include the biosignal detection circuitry mounted on the printed circuit board 232. The biosignal detection circuitry may be electrically connected with the key structure 220 through the connecting member 240.

Figure 5:
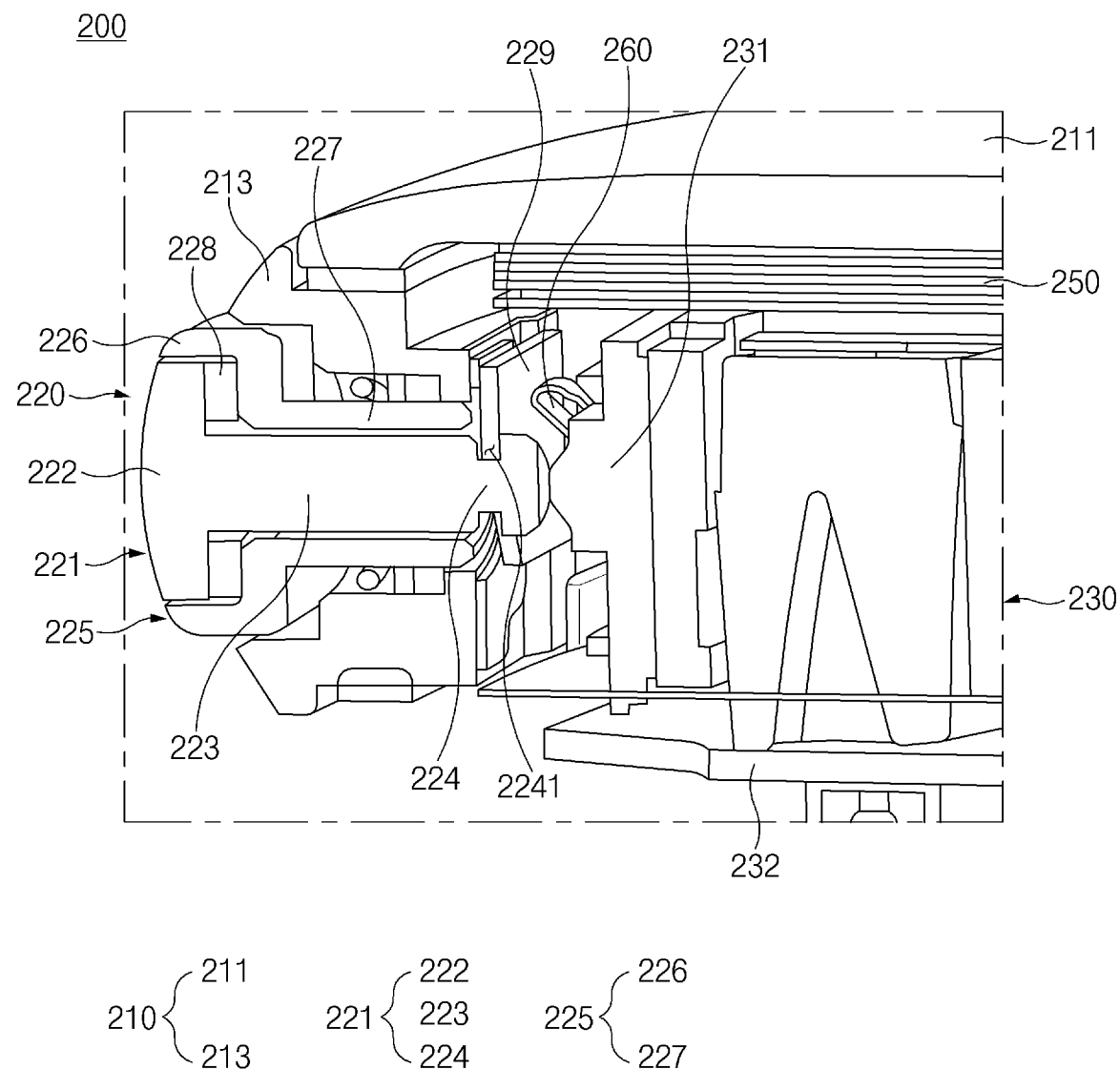
FIG. 5 is a sectional perspective view of the electronic device according to an embodiment.
Figure 6:
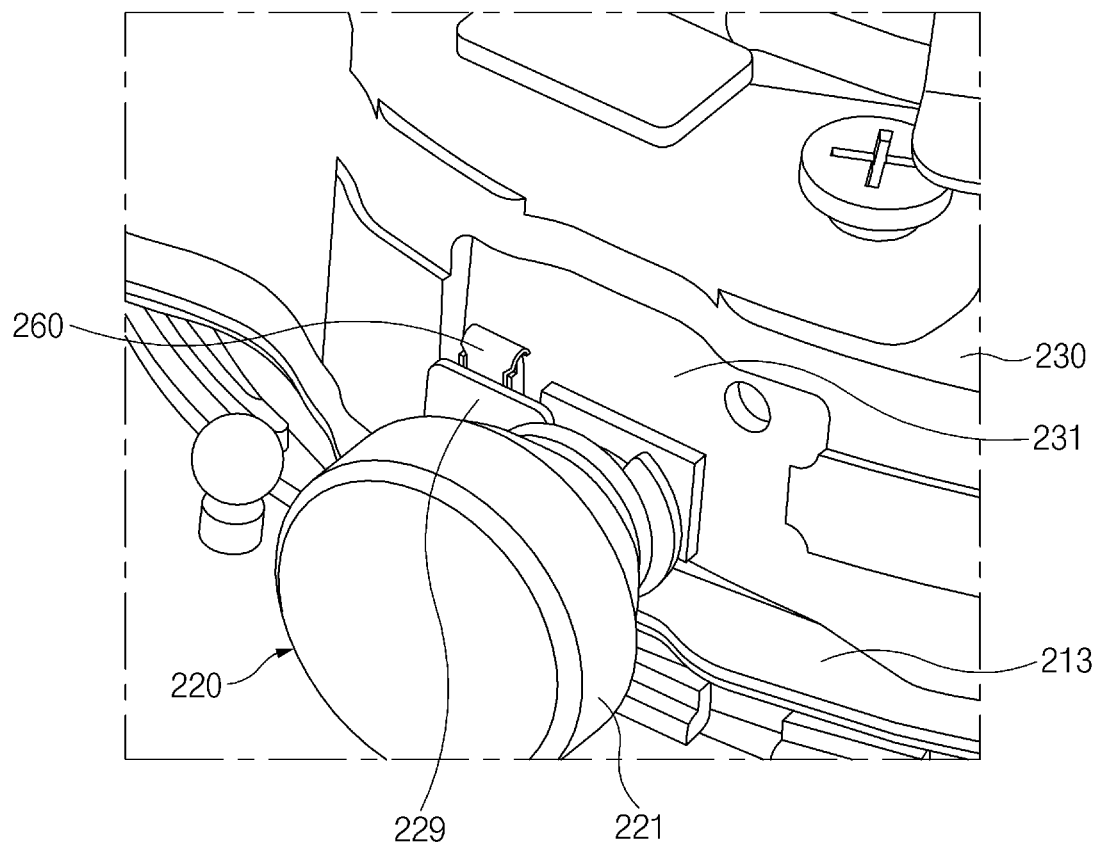
FIG. 6 is a view illustrating a key structure of the electronic device according to an embodiment.

FIG. 5 is a sectional perspective view of the electronic device according to an embodiment. FIG. 5 is a sectional perspective view taken along line A-A' illustrated in FIG. 4. FIG. 6 is a view illustrating the key structure of the electronic device according to an embodiment.

In an embodiment, the electronic device 200 may include a housing 210 and the key structure 220. The housing 210 may include a plurality of members that form surfaces of the electronic device 200. For example, the housing 210 may include a first cover 211 that forms the front surface of the electronic device 200, the bracket 213 that forms the side surface of the electronic device 200, and a second cover (not illustrated) (e.g., a second cover 212 of FIG. 7) that forms the rear surface of the electronic device 200. In certain embodiments, the housing 210 may be referred to as the housing 110 illustrated in FIG. 1.

In an embodiment, the key structure 220 may include the electrode member 221, a support member 225 supporting the electrode member 221, and a fixing member 229 coupled to the electrode member 221.

In an embodiment, the support member 225 may be formed to surround at least part of the electrode member 221. The support member 225 may include a first portion 226 having a first opening formed therein and a second portion 227 having a second opening formed therein. The first opening may be larger than the second opening. The first portion 226 may surround a protruding portion 222 of the electrode member 221, part of an extending portion 223 of the electrode member 221, and a waterproof member 228. A stepped surface may be formed between the first portion 226 and the second portion 227. The waterproof member 228 may be disposed between the stepped surface and the protruding portion 222 of the electrode member 221. The second portion 227 may surround the extending portion 223 of the electrode member 221. The waterproof member 228 may be an O-ring.

In an embodiment, the electrode member 221 may include the protruding portion 222, the extending portion 223 extending from the protruding portion 222 into the bracket 213, and a fixing portion 224 formed on part of the extending portion 223. The protruding portion 222 may be disposed in the first opening of the first portion 226. The extending portion 223 may be disposed in the first opening of the first portion 226 and the second opening of the second portion 227. The fixing portion 224 may be formed on part of the extending portion 223 that is located inside the bracket 213. The fixing portion 224 may include a fixing groove 2241 concavely formed on an outer surface thereof. The fixing portion 224 may be formed to be smaller in size than the extending portion 223. The fixing portion 224 may include stepped surfaces facing each other. The fixing member 229 may be coupled to the fixing groove 2241. The fixing member 229 may be fitted between the stepped surfaces of the fixing portion 224 that face each other.

In an embodiment, the fixing member 229 may be coupled to the fixing portion 224 of the electrode member 221. For example, the fixing member 229 may include an E-ring. The fixing member 229 may be formed of a ring member that is open at one side. The fixing member 229 may be formed to be conductive so as to be electrically connected with the electrode member 221. The fixing member 229 may make contact with a conductive structure 260.

In an embodiment, the conductive structure 260 may be formed to contact the fixing member 229. The conductive structure 260 may be formed on the sidewall 231 of the internal structure 230 and may extend toward the fixing member 229. The conductive structure 260 may be formed such that the electrode member 221 and the fixing member 229 are electrically connected with the printed circuit board 232. In certain embodiments, the conductive structure 260 may include a C-clip. The conductive structure 260 may include a curved area that is bendable to apply an elastic force.

In an embodiment, the electrode member 221 of the key structure 220 may be formed such that the protruding portion 222 has a cross-sectional area corresponding to the first opening of the support member 225 and the extending portion 223 has a cross-sectional area corresponding to the second opening of the support member 225. For example, the electrode member 221 may be formed to be movable to an interior (e.g., the right side with respect to the drawing) and an exterior (e.g., the left side with respect to the drawing) of the housing 210 in a state of being inserted into the openings formed in the support member 225.

In certain embodiments, the cross-sections of the protruding portion 222 and the extending portion 223 may be formed using various shapes. For example, the cross-sections of the protruding portion 222 and the extending portion 223 may be formed in a circular or polygonal (e.g., quadrilateral) shape.

In certain embodiments, the electrode member 221 of the key structure 220 may be formed of a rod member having a substantially circular cross-section. In this case, the diameter of the protruding portion 222 of the electrode member 221 may correspond to the inner diameter of the first opening of the support member 225. The diameter of the extending portion 223 of the electrode member 221 may correspond to the inner diameter of the second opening of the support member 225. The fixing portion 224 of the electrode member 221 may include the fixing groove 2241 formed on part of an outer circumferential surface of the extending portion 223. The fixing portion 224 may have a smaller diameter than the extending portion 223.

In certain embodiments, the electronic device 200 may further include a biosensor (e.g., the sensor module 111 of FIG. 2) that includes an electrode area (e.g., the electrode area 112 of FIG. 1), at least part of which is exposed on a surface of the housing 210, and the biosignal detection circuitry electrically connected with the biosensor and mounted on the printed circuit board 232. In certain embodiments, the biosignal detection circuitry may include a digital circuit that is recoded in a memory so as to be executed by a processor. The biosignal detection circuitry may be electrically connected with the electrode member 221 through the conductive structure 260. The biosignal detection circuitry may be configured to obtain biometric information of a user through the electrode member 221 of the key structure 220. A part of the user's body may make contact with the electrode member 221. In certain embodiments, the biometric information of the user may include information related to the user's heart beat.

Figure 7:
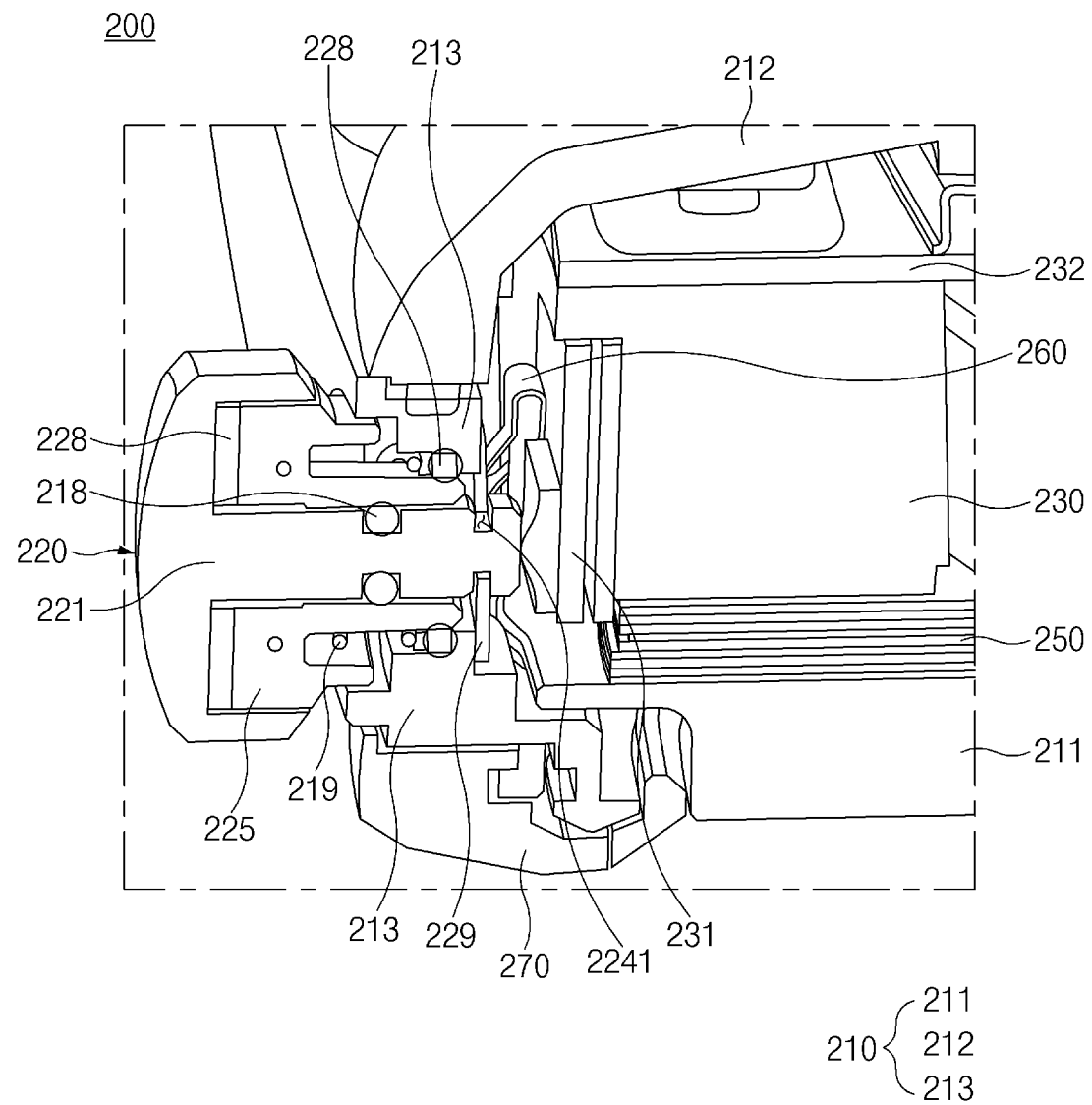
FIG. 7 is a view illustrating a key structure of the electronic device according to certain embodiments.

FIG. 7 is a view illustrating a key structure of the electronic device according to certain embodiments.

Referring to FIG. 7, the electronic device 200 may include the first cover 211 (e.g., the front plate 101 of FIG. 3), the second cover 212 (e.g., the back plate 107 of FIG. 3), the bracket 213, a wheel member 270, the internal structure 230, the printed circuit board 232, a display 250, and the key structure 220. In certain embodiments, the first cover 211, the second cover 212, and the bracket 213 may form the housing 210 (e.g., the housing 110 of FIG. 1).

In certain embodiments, the first cover 211 may form the front surface of the electronic device 200. The first cover 211 may be formed to be transparent such that the display 250 is visible from an exterior of the device. The first cover 211 may have a thick central portion and a thin peripheral portion. The peripheral portion of the first cover 211 may be disposed on a stepped surface of the bracket 213. The display 250, the internal structure 230, and the printed circuit board 232 may be disposed between the first cover 211 and the second cover 212.

In certain embodiments, the display 250 may be disposed between the first cover 211 and the second cover 212. The display 250 may be disposed in the space surrounded by the bracket 213. The display 250 may be disposed on one surface of the internal structure 230. For example, the display 250 may be disposed between the internal structure 230 and the first cover 211, and the printed circuit board 232 may be disposed between the internal structure 230 and the second cover 212.

In certain embodiments, the wheel member 270, together with the first cover 211, may form the front surface of the electronic device 200. The wheel member 270 may be coupled to the bracket 213 so as to be rotatable.

In certain embodiments, the second cover 212 (e.g., the back plate 107 of FIG. 3) may form the rear surface of the electronic device 200. The second cover 212 may be coupled to the bracket 213. The display 250, the internal structure 230, and the printed circuit board 232 may be disposed between the second cover 212 and the first cover 211.

In certain embodiments, the bracket 213 may be formed to surround the space between the first cover 211 and the second cover 212. The bracket 213 may form the side surface of the electronic device 200. The key structure 220 may be coupled to the bracket 213. The bracket 213 may have a through-hole into which at least part of the key structure 220 is inserted.

In certain embodiments, the key structure 220 may include the electrode member 221, the support member 225, and the fixing member 229.

In certain embodiments, the support member 225 may be disposed in the through-hole of the bracket 213. The support member 225 may surround at least part of the electrode member 221 to support rotation of the electrode member 221. One or more bearings 218 may be disposed between the support member 225 and the electrode member 221. The waterproof member 228 may be disposed between the support member 225 and an inner wall of the through-hole of the bracket 213.

In certain embodiments, the electrode member 221 may be coupled to the support member 225 so as to be rotatable. The electrode member 221 may form part of the side surface of the electronic device 200. The electrode member 221 may extend from the outside to the inside of the bracket 213 through the through-hole of the bracket 213. The electrode member 221 may be surrounded by the support member 225. The electrode member 221 may be rotatably coupled with the support member 225 through the bearings 218. The electrode member 221 may include a first end portion exposed on the side surface of the electronic device 200 and a second end portion facing the internal structure 230. The second end portion of the electrode member 221 may be located in the interior space of the bracket 213. The fixing member 229 may be coupled to the second end portion of the electrode member 221. The electrode member 221 may have, on the second end portion thereof, the fixing groove 2241 into which the fixing member 229 is inserted.

In certain embodiments, the support member 225 and the bracket 213 may be connected by an elastic member 219. One side of the elastic member 219 may be connected to the support member 225, and an opposite side of the elastic member 219 may be connected to the bracket 213. Accordingly, the electrode member 221, together with the support member 225, may move in a direction toward the inside of the housing 210 or an opposite direction thereto. For example, when the electrode member 221 and the support member 225 move toward the inside of the housing 210 (e.g., toward the bracket 213), the elastic member 219 may be compressed. The compressed elastic member 219 may apply an elastic force to the electrode member 221 and the support member 225 in a direction toward the outside of the housing 210 (e.g., a direction away from the bracket 213). Accordingly, the key structure 220 may provide a rotational operation and a push operation.

In certain embodiments, the fixing member 229 may have a larger cross-sectional area than the through-hole of the bracket 213. The fixing member 229 may be coupled to the second end portion of the electrode member 221. For example, the fixing member 229 may include an E-ring inserted into the fixing groove 2241 of the electrode member 221. For example, the fixing member 229 may be formed of a ring member that is open at one side. The fixing member 229 may be formed to be conductive so as to be electrically connected with the electrode member 221. At least part of the fixing member 229 may make contact with the conductive structure 260.

In certain embodiments, the fixing member 229 may prevent the electrode member 221 from deviating in the direction of an axis of rotation. For example, the fixing member 229 may be inserted into the fixing groove 2241 formed on the outer surface of the electrode member 221 and may not restrict rotation of the electrode member 221. However, the fixing member 229, which is formed to be larger than the through-hole of the bracket 213, may prevent the electrode member 221 from deviating through the through-hole of the bracket 213.

In certain embodiments, the electronic device 200 may further include the biosignal detection circuitry mounted on the printed circuit board 232. The biosignal detection circuitry may be electrically connected with the electrode member 221 through the conductive structure 260. The biosignal detection circuitry may be configured to obtain biometric information of a user through the electrode member 221 of the key structure 220. A part of the user's body may make contact with the electrode member 221. In certain embodiments, the biometric information of the user may include information related to the user's heart beat.

Figure 8:
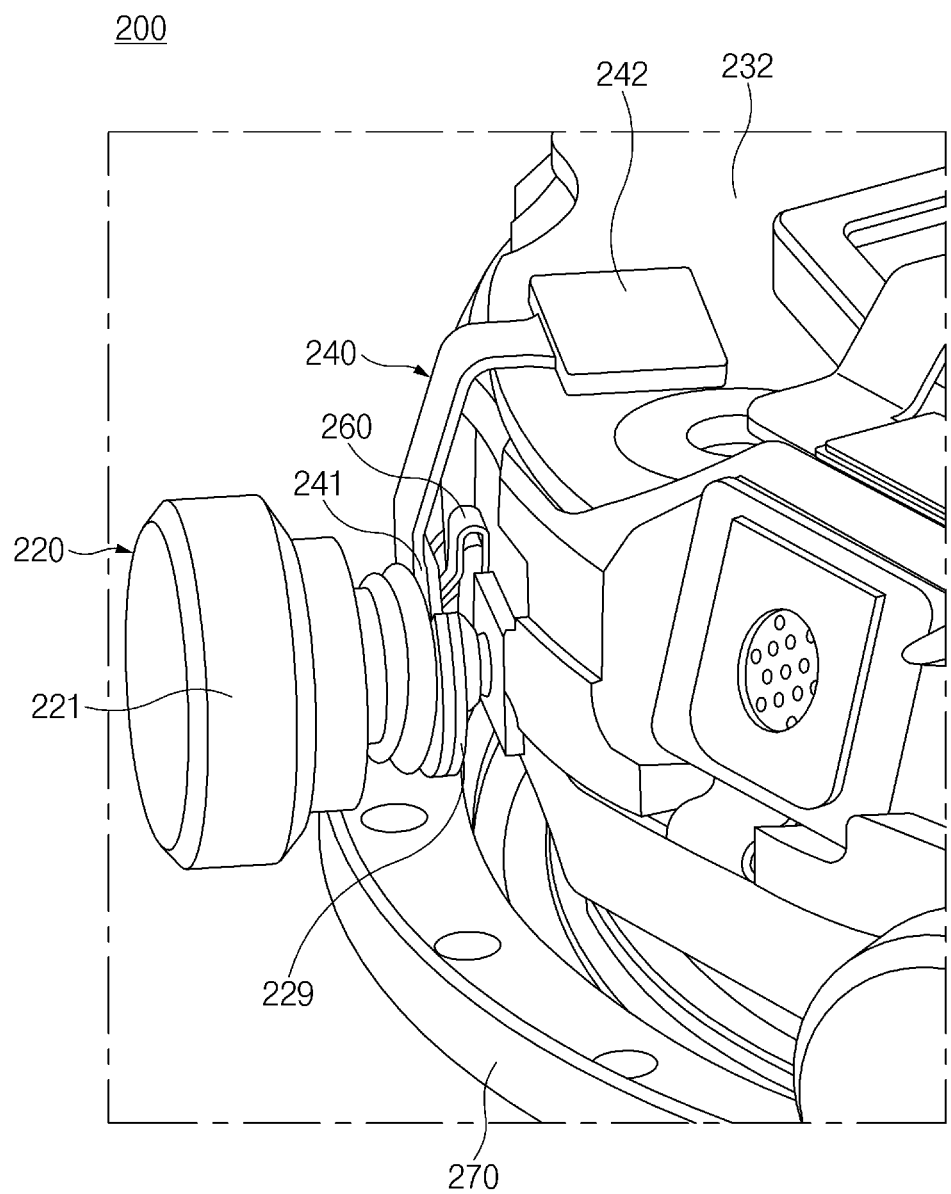
FIG. 8 is a view illustrating a key structure of the electronic device according to certain embodiments.
Figure 9:
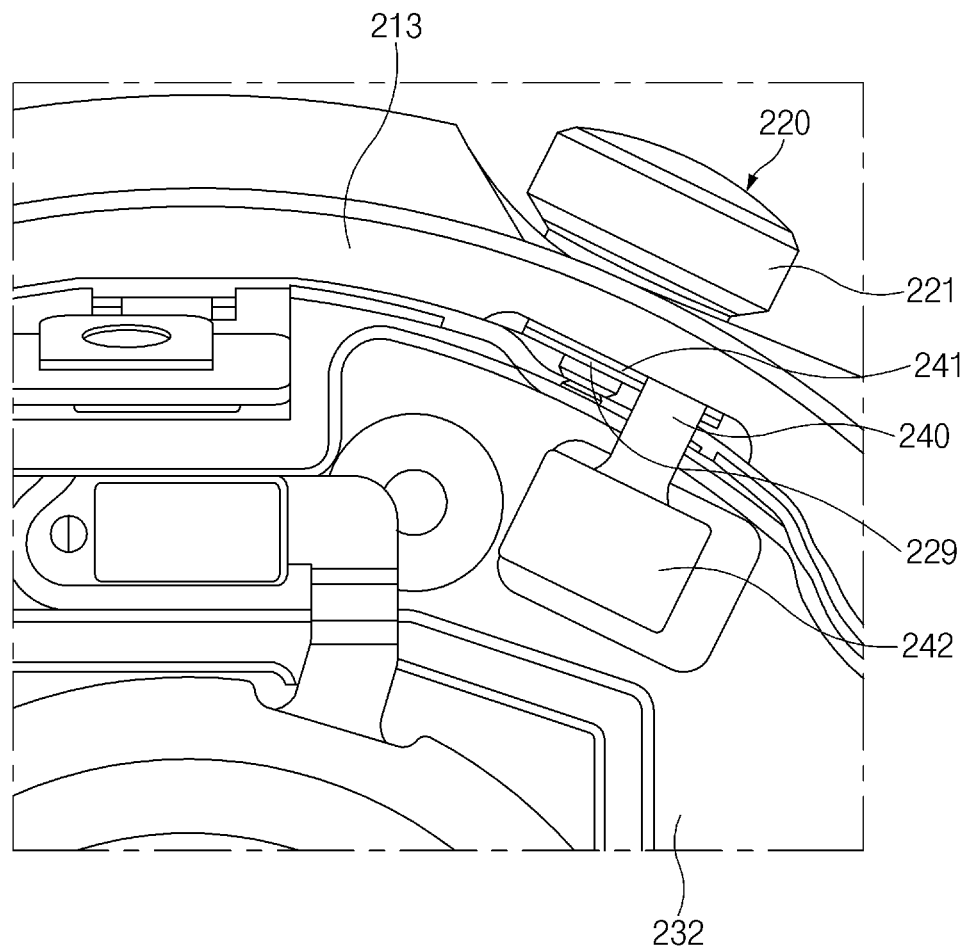
FIG. 9 is a view illustrating the key structure of the electronic device according to certain embodiments.

FIG. 8 is a view illustrating a key structure of the electronic device according to certain embodiments. FIG. 9 is a view illustrating the key structure of the electronic device according to certain embodiments.

Referring to FIG. 8, the electronic device 200 may further include the connecting member 240 connecting the electrode member 221 of the key structure 220 and the printed circuit board 232. The connecting member 240 may include a conductive area (e.g., a first connector 241) that is connected with the fixing member 229 and a signal line (not illustrated) that extends from the conductive area to the printed circuit board 232.

In certain embodiments, the connecting member 240 may include the first connector 241 electrically connected with the fixing member 229 and a second connector 242 electrically connected with the printed circuit board 232.

In certain embodiments, the connecting member 240 may be implemented with a flexible printed circuit board including the signal line (not illustrated) that connects the first connector 241 and the second connector 242.

In certain embodiments, the electronic device 200 may further include a conductive structure (e.g., the conductive structure 260 of FIG. 7) that electrically connects the fixing member 229 and the printed circuit board 232. Accordingly, the electrode member 221 may be electrically connected with a sensor and a processor on the printed circuit board 232 through the conductive structure 260 in addition to the connecting member 240.

In certain embodiments, the connecting member 240 may include an insulating layer and a conductive pattern at least partially surrounded by the insulating layer. In this case, the conductive area (e.g., the first connector 241) that contacts the fixing member 229 may include an area formed by exposing the conductive pattern by removing part of the insulating layer.

Figure 10:
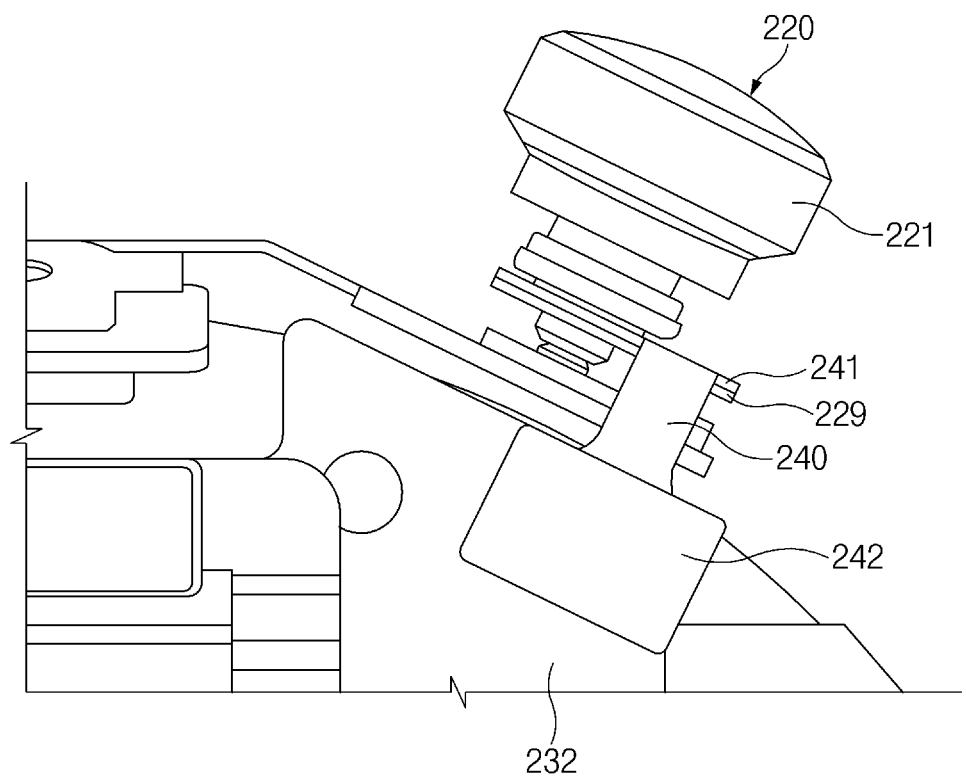
FIG. 10 is a view illustrating the key structure of the electronic device according to certain embodiments.

FIG. 10 is a view illustrating the key structure of the electronic device according to certain embodiments. FIG. 10 is a view in which the bracket is omitted from the electronic device illustrated in FIG. 9.

In an embodiment, the electronic device 200 may include the bracket 213, the key structure 220, the connecting member 240, the internal structure 230, and the printed circuit board 232.

In certain embodiments, the bracket 213 may form a surface of the electronic device 200. The internal structure 230 may be disposed in the interior space of the bracket 213. The printed circuit board 232 may be disposed on the internal structure 230. In certain embodiments, the bracket 213 may form part of the housing 210. The bracket 213 may be coupled with the key structure 220 such that part of the key structure 220 protrudes from the surface of the electronic device 200 and the remaining part of the key structure 220 extends into the interior space of the bracket 213.

In certain embodiments, the key structure 220 may include the electrode member 221, the fixing member 229 for fixing the electrode member 221, and the connecting member 240 for electrically connecting the fixing member 229 and the printed circuit board 232. The fixing member 229 may be conductive. The fixing member 229 may be formed of a ring member surrounding at least part of the outer surface of the electrode member 221. The fixing member 229 may be formed of a ring member that is open at one side. For example, the fixing member 229 may include an E-ring.

In certain embodiments, the connecting member 240 may include the first connector 241 connected to the fixing member 229 and the second connector 242 connected to the printed circuit board 232. For example, the connecting member 240 may include a flexible printed circuit board. The first connector 241, together with the fixing member 229, may be disposed in the fixing groove 2241 formed on the outer surface of the electrode member 221. The first connector 241, together with the fixing member 229, may be fitted into the fixing groove 2241.

In certain embodiments, the first connector 241 may include a conductive area making contact with the fixing member 229 and a non-conductive area facing away from the conductive area. The non-conductive area may include an insulating tape. Accordingly, the connecting member 240 may be electrically connected with the fixing member 229, but may be electrically insulated from a different structure (e.g., the bracket 213) of the electronic device 200.

In certain embodiments, the electronic device 200 may further include the biosignal detection circuitry mounted on the printed circuit board 232. The biosignal detection circuitry may be electrically connected with the electrode member 221 through the connecting member 240. The biosignal detection circuitry may be configured to obtain biometric information of a user through the electrode member 221 of the key structure 220. A part of the user's body may contact the electrode member 221. In certain embodiments, the biometric information of the user may include information related to the user's heart beat.

Figure 11:
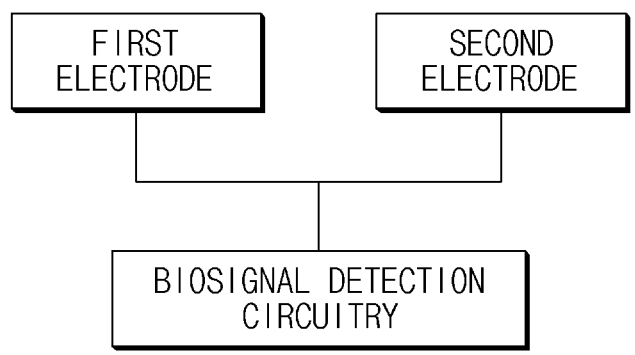
FIG. 11 is a view illustrating a user biometric information acquisition system of an electronic device according to an embodiment.

FIG. 11 is a view illustrating a user biometric information acquisition system of an electronic device according to an embodiment.

Referring to FIG. 11, the electronic device may include a first electrode, a second electrode, and biosignal detection circuitry. The first electrode and the second electrode may be exposed on external surfaces of the electronic device, respectively. The first electrode may be referred to as the electrode member 221 illustrated in FIGS. 4 to 10. The second electrode may be referred to as the sensor module 111 illustrated in FIG. 2.

In certain embodiments, the first electrode may be exposed on a side surface of the electronic device. The second electrode may be exposed on a rear surface of the electronic device. For example, the first electrode may be referred to as the first electrode area 112 illustrated in FIG. 1. For example, the second electrode may be referred to as the second electrode area 113 and/or the third electrode area 114 illustrated in FIG. 2. For example, the second electrode may include a plurality of electrodes (e.g., the second electrode area 113 and the third electrode area 114 of FIG. 2).

Parts of a user's body may contact the first electrode and the second electrode, respectively. For example, a wrist of the user may contact the second electrode. Another body part (e.g., a finger) rather than the user's wrist may contact the first electrode.

Accordingly, the first electrode, the second electrode, and the user's body may configure one closed circuit.

In an embodiment, the biosignal detection circuitry may be configured to obtain biometric information of the user based on the first electrode and the second electrode. The biometric information of the user may include information related to the user's heart beat.

In certain embodiments, the biometric information of the user may include at least one of an electrocardiogram (ECG), a galvanic skin response (GSR), an electroencephalogram (EEG), or a bioimpedence assessment (BIA).

The electronic device 200 according to the embodiments of the disclosure may include the electrode member 221 not affecting wireless communication performance of an antenna (e.g., the antenna 131 of FIG. 3). For example, the electrode member 221 may be formed on an area (e.g., the side surface of the electronic device 200) that is not included in a main radiation direction of the antenna (e.g., the direction toward the front surface of the electronic device 200).

An electronic device 200 may include a housing 210 including a first surface 110A that forms a front surface of the electronic device 200, a second surface 110B that faces away from the first surface 110A, and a side surface 110C that surrounds an interior space between the first surface 110A and the second surface 110B, a key structure 220 that forms part of the side surface 110C and extends into the interior space and that includes an electrode member 221, part of which is exposed on the side surface 110C, the electrode member 221 extending into the interior space, a display 250 disposed in the housing 210 so as to be visually exposed through the first surface 110A, an internal structure 230 that is disposed between the display 250 and the second surface 110B and that includes a printed circuit board, and a conductive structure 260 that protrudes from the internal structure 230 and that is electrically connected with the electrode member 221 of the key structure 220.

In certain embodiments, the conductive structure 260 may include a C-clip.

In certain embodiments, the conductive structure 260 may include a flexible printed circuit board.

In certain embodiments, the flexible printed circuit board may include an insulating layer, a conductive pattern at least partially surrounded by the insulating layer, and a conductive area that makes contact with the electrode member, and the conductive area is formed by exposing the conductive pattern by removing part of the insulating layer.

In certain embodiments, the electronic device may further include a biosensor including an electrode area 112, 113, or 114 exposed on at least part of a surface of the housing 210 and biosignal detection circuitry disposed on the printed circuit board 132 and electrically connected with the biosensor, and the biosignal detection circuitry may be configured to obtain biometric information of a user, based on electrical signals received from the electrode member 221 and the electrode area 112, 113, or 114, respectively.

In certain embodiments, the biometric information may include electrocardiogram information of the user.

In certain embodiments, the electronic device may further include a flexible printed circuit board extending from the conductive structure 260 to the printed circuit board.

In certain embodiments, the electronic device may further include a wheel member 270 disposed on the first surface 110A and coupled with the housing 210 so as to be rotatable.

In certain embodiments, the electrode member 221 may protrude from the side surface of the electronic device.

In certain embodiments, the housing 210 may have, in the side surface thereof, a through-hole in which the electrode member 221 is disposed, and the key structure 220 may further include a support member 225 disposed in the through-hole and formed to surround the electrode member 221.

In certain embodiments, the key structure 220 may further include a waterproof member 228 disposed between the through-hole and the support member 225.

In certain embodiments, the electrode member 221 may be configured to rotate relative to the support member 225, and the key structure 220 may further include a bearing 218 disposed between the support member and the electrode member 221.

In certain embodiments, the electrode member 221 may include a fixing groove 2241 concavely formed on an outer surface of the electrode member, the key structure 220 may further include a fixing member 229 that fixes the electrode member 221, and the fixing member 229 may include a ring member inserted into the fixing groove.

In certain embodiments, the fixing member 229 may be formed to be conductive, and the conductive structure 260 may make contact with the fixing member 229 so as to be electrically connected with the electrode member 221.

In certain embodiments, the display 250 may be disposed between the internal structure 230 and the first surface 110A, and the printed circuit board 232 may be disposed between the internal structure 230 and the second surface 110B.

In certain embodiments, the electrode member 221 may include a fixing groove 2241 concavely formed on an outer surface of the electrode member, the conductive structure 260 may include a flexible printed circuit board, and the key structure 220 may further include a fixing member 229 inserted into the fixing groove 2241 together with the flexible printed circuit board to fix the electrode member 221.

In certain embodiments, the flexible printed circuit board may include a conductive area that makes contact with the fixing member.

In certain embodiments, the electronic device may further include a first cover 211 that forms the first surface 110A of the housing 210, a second cover 212 that forms the second surface 110B of the housing 210, and a bracket 213 that forms the side surface 110C of the housing 210, and the bracket 213 may have a through-hole in which at least part of the key structure 220 is disposed.

In certain embodiments, the key structure 220 may further include a support member 225 disposed between the through-hole and the electrode member 221. The support member 225 may include a first portion including a first opening having a first diameter and a second portion including a second opening having a second diameter smaller than the first diameter. The electrode member 221 may include a protruding portion 222 disposed in the first opening and an extending portion 223 extending from the protruding portion 222 into the interior space of the housing 210 through the inside of the second opening. The protruding portion 222 may protrude from the side surface of the housing 210 such that a part of a user's body is able to make contact with the protruding portion.

In certain embodiments, the extending portion 223 may include a first end portion connected with the protruding portion 222 and a second end portion located in the interior space of the housing 210. The key structure 220 may further include a fixing member 229 that includes a fixing ring and that is coupled to the second end portion, and the conductive structure 260 may make contact with the fixing member 229.

According to the embodiments, the disclosure may provide a wearable electronic device that includes an externally exposed electrode for an electrocardiogram sensor and that is capable of efficiently using an interior space and preventing deterioration in antenna performance.

In addition, the disclosure may provide various effects that are directly or indirectly recognized.

Certain embodiments of the disclosure and terms used herein are not intended to limit the technologies described in the disclosure to specific embodiments, and it should be understood that the embodiments and the terms include modification, equivalent, and/or alternative on the corresponding embodiments described herein. With regard to description of drawings, similar components may be marked by similar reference numerals. The terms of a singular form may include plural forms unless otherwise specified. In the disclosure disclosed herein, the expressions "A or B", "at least one of A and/or B", "A, B, or C", or "at least one of A, B, and/or C", and the like used herein may include any and all combinations of one or more of the associated listed items. Expressions such as "first," or "second," and the like, may express their components regardless of their priority or importance and may be used to distinguish one component from another component but is not limited to these components. When an (e.g., first) component is referred to as being "(operatively or communicatively) coupled with/to" or "connected to" another (e.g., second) component, it may be directly coupled with/to or connected to the other component or an intervening component (e.g., a third component) may be present.

According to the situation, the expression "adapted to or configured to" used herein may be interchangeably used as, for example, the expression "suitable for", "having the capacity to", "changed to", "made to", "capable of" or "designed to" in hardware or software. The expression "a device configured to" may mean that the device is "capable of" operating together with another device or other parts. For example, a "processor configured to (or set to) perform A, B, and C" may mean a dedicated processor (e.g., an embedded processor) for performing corresponding operations or a generic-purpose processor (e.g., a central processing unit (CPU) or an application processor (AP)) which performs corresponding operations by executing one or more software programs which are stored in a memory device (e.g., the memory).

The term "module" used herein may include a unit, which is implemented with hardware, software, or firmware, and may be interchangeably used with the terms "logic", "logical block", "part", "circuit", or the like. The "module" may be a minimum unit of an integrated part or a part thereof or may be a minimum unit for performing one or more functions or a part thereof. The "module" may be implemented mechanically or electronically and may include, for example, an application-specific IC (ASIC) chip, a field-programmable gate array (FPGA), and a programmable-logic device for performing some operations, which are known or will be developed.

At least a part of an apparatus (e.g., modules or functions thereof) or a method (e.g., operations) according to certain embodiments may be, for example, implemented by instructions stored in a computer-readable storage media (e.g., the memory) in the form of a program module. The instruction, when executed by a processor (e.g., the processor), may cause the processor to perform a function corresponding to the instruction. The computer-readable recording medium may include a hard disk, a floppy disk, a magnetic media (e.g., a magnetic tape), an optical media (e.g., a compact disc read only memory (CD-ROM) and a digital versatile disc (DVD), a magneto-optical media (e.g., a floptical disk)), an embedded memory, and the like. The one or more instructions may contain a code made by a compiler or a code executable by an interpreter.

Each component (e.g., a module or a program module) according to certain embodiments may be implemented using a single entity or a plurality of entities, a part of the above-described sub-components may be omitted, or other sub-components may be further included. Alternatively or additionally, after being integrated in one entity, some components (e.g., a module or a program module) may identically or similarly perform the function executed by each corresponding component before integration. According to certain embodiments, operations executed by modules, program modules, or other components may be executed by a successive method, a parallel method, a repeated method, or a heuristic method, or at least one part of operations may be executed in different sequences or omitted. Alternatively, other operations may be added.

While the disclosure has been shown and described with reference to certain embodiments thereof, it will be understood by those skilled in the art that various changes in form and details may be made therein without departing from the disclosure as defined by the appended claims and their equivalents.

What is claimed is:

1. An electronic device, comprising:
    a housing including a first surface forming a front surface of the electronic device, a second surface facing away from the first surface, and a side surface surrounding an interior space defined between the first surface and the second surface;
    a key structure forming part of the side surface and extending into the interior space, the key structure including an electrode member partially exposed to an exterior environment, wherein the electrode member partially extends into the interior space and includes an end portion located in the interior space;
    a conductive fixing member fitted into a groove formed in the end portion of the electrode member;
    a display disposed in the housing so as to be visible through the first surface from the exterior environment;
    an internal structure disposed between the display and the second surface, wherein the internal structure includes a printed circuit board;
    a conductive structure protruding from the internal structure to contact the conductive fixing member, wherein the conductive structure is electrically connected with the electrode member of the key structure;
    a flexible printed circuit board including:
        a first connector fitted into the groove of the end portion of the electrode member and disposed on the conductive fixing member,
        a second connector disposed on the printed circuit board, and
        conductive traces extending from the first connector to the second connector, and electrically connecting the conductive fixing member to the printed circuit board; and
    at least one processor disposed on the printed circuit board, wherein the at least one processor is electrically connected to the electrode member via;
    a first path at least partially defined by the conductive structure and the conductive fixing member, and
    a second path at least partially defined by the conductive traces of the flexible printed circuit board and the conductive fixing member.

2. The electronic device of claim 1, wherein the conductive structure includes a C-clip.

3. The electronic device of claim 1, wherein the conductive structure includes a second flexible printed circuit board.

4. The electronic device of claim 3, wherein the flexible printed circuit board includes an insulating layer, a conductive pattern at least partially surrounded by the insulating layer, and a conductive area contacting the electrode member, and wherein the conductive area is formed by exposing the conductive pattern via removal of part of the insulating layer.

5. The electronic device of claim 1, further comprising:
    a biosensor including an electrode area disposed on at least part of a surface of the housing and exposed to the exterior environment; and
    biosignal detection circuitry disposed on the printed circuit board and electrically connected with the biosensor,
    wherein the biosignal detection circuitry is configured to obtain biometric information of a user, based on electrical signals received from the electrode member and the electrode area, respectively.

6. The electronic device of claim 5, wherein the biometric information includes electrocardiogram information of the user.

7. The electronic device of claim 1, further comprising:
    a wheel member disposed on the first surface and coupled with the housing so as to be rotatable.

8. The electronic device of claim 1, wherein the electrode member protrudes from the side surface of the electronic device.

9. The electronic device of claim 1, wherein the housing includes, in the side surface thereof, a through-hole in which the electrode member is disposed, and
   wherein the key structure further includes a support member disposed in the through-hole and formed as to surround the electrode member.

10. The electronic device of claim 9, wherein the key structure further includes a waterproof member disposed between the through-hole and the support member.

11. The electronic device of claim 9, wherein the electrode member is configured to rotate relative to the support member, and
   wherein the key structure further includes a bearing disposed between the support member and the electrode member.

12. The electronic device of claim 1, wherein the display is disposed between the internal structure and the first surface, and
   wherein the printed circuit board is disposed between the internal structure and the second surface.

13. The electronic device of claim 1, further comprising:
   a first cover forming the first surface of the housing;
   a second cover forming the second surface of the housing; and
   a bracket forming the side surface of the housing,
   wherein the bracket includes a through-hole in which at least part of the key structure is disposed.

14. The electronic device of claim 13, wherein the key structure further includes a support member disposed between the through-hole and the electrode member,
   wherein the support member includes a first portion including a first opening having a first diameter, and a second portion including a second opening having a second diameter smaller than the first diameter,
   wherein the electrode member includes a protruding portion disposed in the first opening and an extending portion extending from the protruding portion into the interior space of the housing through the inside of the second opening, and
   wherein the protruding portion protrudes from the side surface of the housing to allow contact of a user's body part with the protruding portion.

15. The electronic device of claim 14, wherein the extending portion includes a first end portion connected with the protruding portion, and a second the end portion located in the interior space of the housing,
   wherein the conductive fixing member includes a fixing ring.

\* \* \* \* \*